United States Patent
Kiuru et al.

(10) Patent No.: US 6,522,720 B1
(45) Date of Patent: Feb. 18, 2003

(54) METHOD TO MEASURE THE RELATIVE PERFUSION OF THE LUNGS

(76) Inventors: Aaro Kiuru, Honkatie 28/8, FIN-20540, Turku (FI); Erkki Svedström, Varputie 5, FIN-23100, Mynamaki (FI)

( * ) Notice: Subject to any disclaimer, the term of this patent is extended or adjusted under 35 U.S.C. 154(b) by 0 days.

(21) Appl. No.: 09/555,247
(22) PCT Filed: Sep. 24, 1999
(86) PCT No.: PCT/FI99/00785
§ 371 (c)(1),
(2), (4) Date: Aug. 11, 2000
(87) PCT Pub. No.: WO00/18299
PCT Pub. Date: Apr. 6, 2000

(30) Foreign Application Priority Data

Sep. 29, 1998 (FI) .................................................. 982103

(51) Int. Cl.$^7$ ................................................. A61B 5/08
(52) U.S. Cl. ........................................... 378/95; 378/42
(58) Field of Search ........................... 378/95, 42, 8, 378/98.12, 62

(56) References Cited

U.S. PATENT DOCUMENTS

| | | | |
|---|---|---|---|
| 4,709,385 A | * 11/1987 | Pfeiler et al. | ............ 378/98.12 |
| 4,729,379 A | * 3/1988 | Ohe | ......................... 378/98.12 |
| 4,868,747 A | 9/1989 | Mori et al. | |
| 4,939,757 A | 7/1990 | Nambu | |
| 5,630,414 A | * 5/1997 | Horbaschek | .................. 378/62 |

FOREIGN PATENT DOCUMENTS

JP              60050900         7/1985

* cited by examiner

Primary Examiner—Drew A. Dunn
(74) Attorney, Agent, or Firm—Skinner and Associates

(57) ABSTRACT

The invention covers a method to determine the relative lung perfusion image with the fluoroscopic principle. Transmitted X-ray radiation through the lungs of the patient under examination is measured at least during one heart cycle. An image intensifier is used to collect the images which are digitized, taken to the apparatus and further analyzed. The results are the grey scale image and numerical map depicting the lung perfusion distribution.

5 Claims, 3 Drawing Sheets

METHOD TO MEASURE THE RELATIVE PERFUSION OF THE LUNGS

BACKGROUND OF THE INVENTION

This invention deals with a method to measure the perfusion of the lungs in fluoroscopy in which it is possible to obtain the result as a numerical map which shows the perfusion normalised to the maximum value in the map.

Many different methods have been and are used to measure and evaluate different parameters of the function of the lungs. Methods possess considerable differences both in the performance and other factors like general requirements, pain and inconvenience to the patient, duration of the measurements, patient radiation dose.

Pulmonary embolism (PE) refers to the total or partial blockage of blood circulation in pulmonary arteries, and the seriousness is connected to the extend of the blockage. The diagnosis of PE is an important procedure in terms of the prognosis of the patient. An non-diagnosed PE may cause the death of the patient with the probability of about 30%, while when treated with anticoagulation it is 8%. Pulmonary embolism is, therefore, diagnosed based on the information obtained from nuclear medicine ventilation-perfusion scans, high resolution computed tomography HRCT or pulmonary angiography. The last method, pulmonary angiography is used to lesser extent due to its invasive nature and often poor availability. Scintigraphic ventilation-perfusion scans are most commonly used, but the interpretation of the examination may be ambiguous. The recently widely used method is CT imaging with contrast infusion in the spiral mode.

Information of different methods describe the lung function from different aspects, therefore different methods complement each other.

BRIEF SUMMARY OF THE INVENTION

The goal of this invention is to set up a method in which a clear image is obtained of the conditions of lung perfusion. The examination is fast with no invasive interventions and with only a small radiation dose to the patient. The goal is achieved as is said to be characteristic to the invention in the accompanying claims.

The invention is described more accurately in the following using the enclosed drawings:

DETAILED DESCRIPTION OF THE INVENTION

Figure 1:
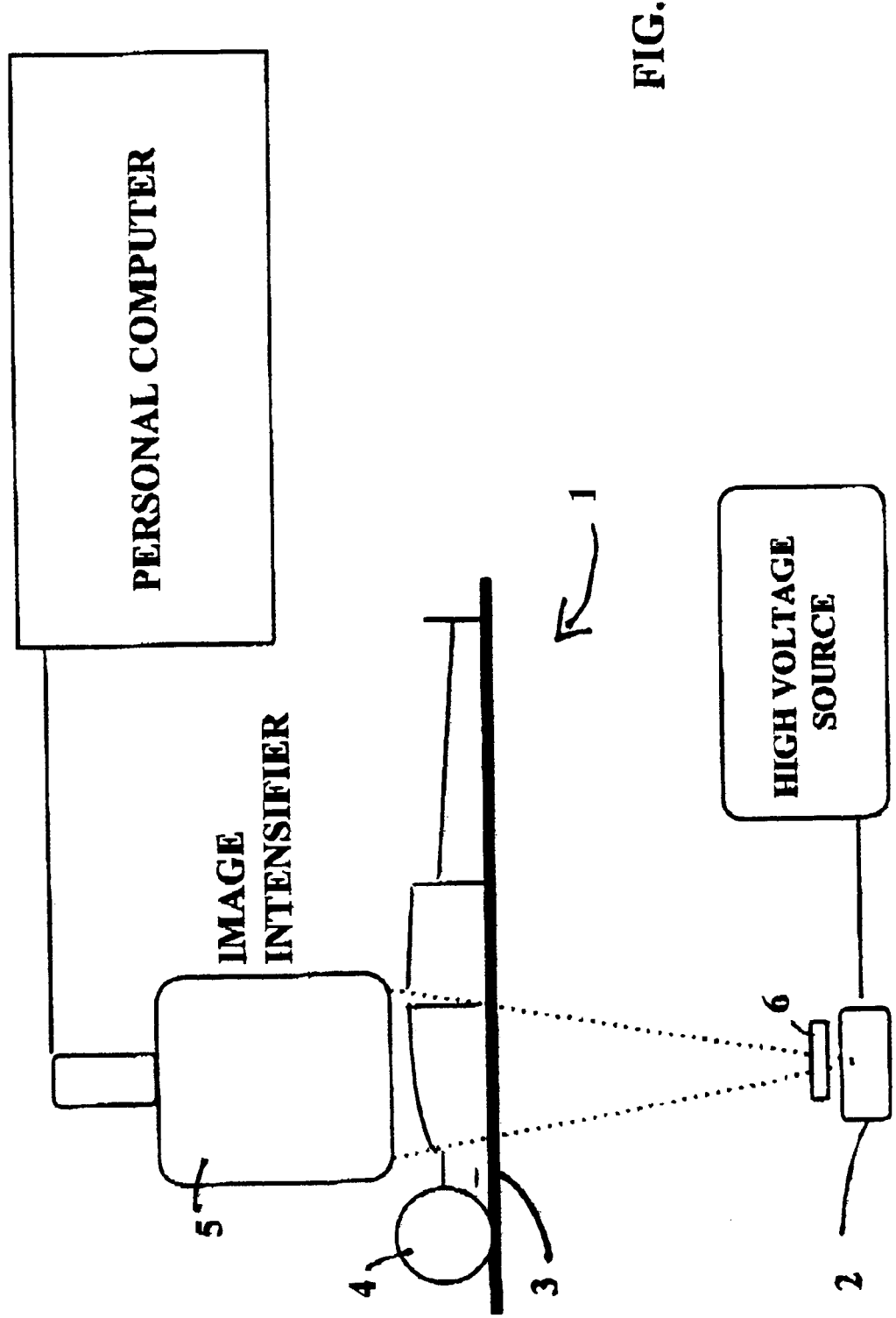
FIG. 1 depicts a general view of the apparatus in use.
Figures 2A, 2B:
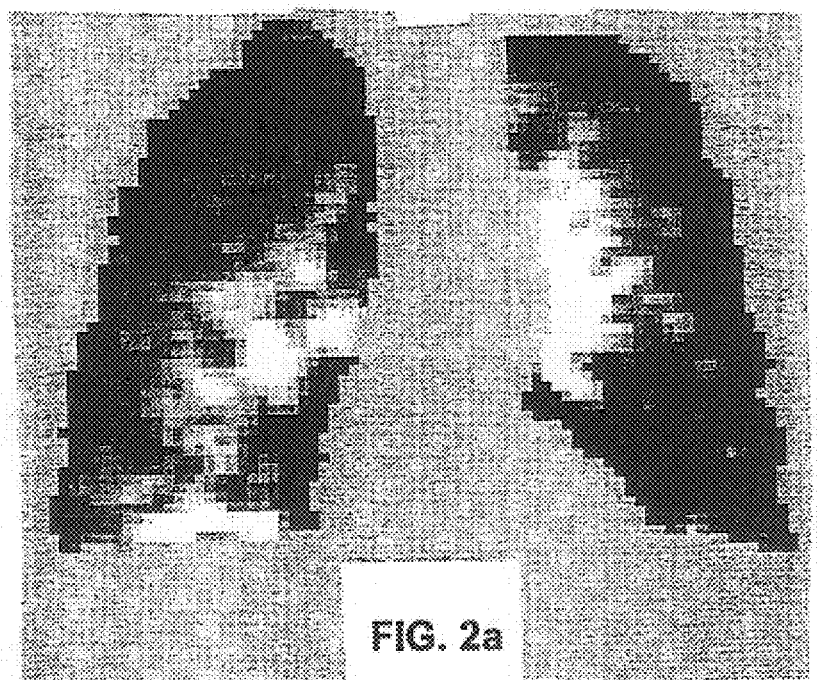
FIGS. 2a and 2b show the grey scale image and corresponding numerical map of the perfusion of the lungs of a healthy volunteer made with imaging method of the invention.
Figure 3A:
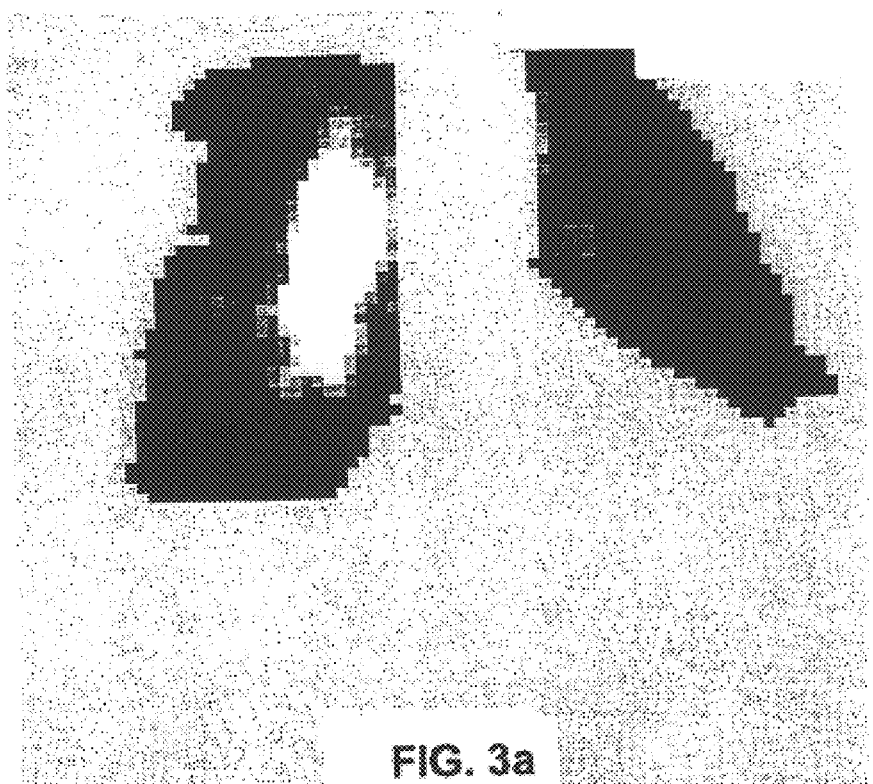
FIGS. 3a and 3b show the corresponding images of a sick patient.
Figure 3B:
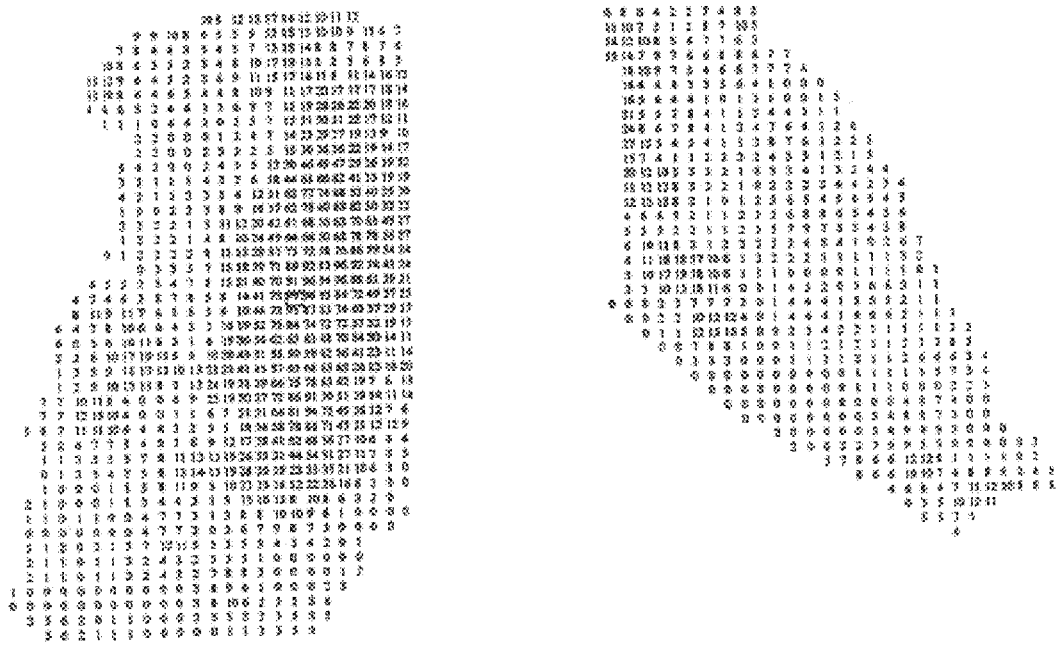

The method of the invention is described in the following while referring to the figures. FIG. 1 shows the simplified apparatus. The apparatus 1 is made of the radiation source, for instance an X-ray tube 2 with about 100 kVp which emits the radiation beam towards the patient 4 lying on the bed 3. The apparatus includes also a filter or filters 6 in the usual way. The radiation beam is detected with an image intensifier tube 5 and the gathered data is collected with for example a Personal Computer (PC) device for further handling and analysis.

During the imaging the patient has to hold his breath, at least during one heart cycle. Also a patient in a fairly poor health condition can make this. As mentioned earlier no interventions are performed to the patient, the method is fully non-invasive, no radioactive isotopes or contrast media is used. The method is fast and advantageous in use.

Describing in greater detail the apparatus and the method function in the following way. High voltage of about 100 kVp with a fixed fluoroscopic mA-value and a copper filter of approximate thickness 1 to 3 mm are used in imaging. High voltage is varied depending on patient size. Otherwise fluoroscopic parameters are kept constant during the study. The varying X-ray transmission caused by pulmonary perfusion are recorded.

The patient dose is approximately equal to a conventional chest X-ray examination. The result of the imaging is perspicuous, in nearly complete non-visualisation of ribs, but clavicles may on the other hand diminish somewhat the visualisation of lung apices.

A series of digital images usually 50 or 100 with 256 grey shades are collected at 12.5 or 25 Hz. Generally the matrix size of 384×288 is used.

The images are analyzed in different ways after the collection of the data. The original and subtracted image series and parametric images like the images of the amplitude, asynchrony and perfusion are produced and animated, and quantitative curves and values from user selected ROI-areas are calculated. In the subtraction mode the average image of a series consisting of one or several perfusion cycles can be used. The development and analysis of perfusion images collected while holding the breath requires dedicated, careful analysis, because intensity changes caused by perfusion and partly by the movements of blood vessels and lung tissues are quite small.

The aim of this invention is to measure quantitatively local lung pulsation in PA projection. The perfusion (blood pulsation) signal in the lung parenchyma is weak, weakest in the periphery, being in the range of 1–2 units when the image noise is 20 approximately 0.2–0.5 units. The measured perfusion images demonstrate local and temporal changes in the X-ray transmission through the lungs, caused by changes of the blood content and corresponding density changes of the lung parenchyma. Local variations in user selected subareas are processed. Cycling pulses are seen in curves from selected ROI-areas and faintly also in the animation of subtracted images. The phase differences between different ROI areas are minor facilitating the following analysis in normal subjects.

The perfusion images are analyzed interactively roughly in the following way. The analysis starts by animating the measured images to ascertain that the diaphragm of the patient does not move. The program draws border lines to the lungs which can also, when necessary, be corrected manually. The user selects a ROI area anywhere in the middle of either lungs. The user marks two or more minima points in the thereby calculated perfusion curve which may be the original or for instance a three-point time averaged curve.

The interpreter selects the size of a submatrix usually between 1×1–6×6 pixels, possibly up to 16×16 which will be used in the calculation of local pulsations from the entire image series. A parametric perfusion image is constructed of the summed areas of these pulsations using the selected time points. The normalized grey scale perfusion image and corresponding numerical map(s) are displayed and printed out. The highest value found inside the lungs in the numerical map is normalized to 100 units. ROI-technique can further be utilized to analyze and quantitatively compare lung regions.

The pulsation in the aorta which is at the same phase with lung pulsation must in most cases be excluded to facilitate the proper normalization of the perfusion images. Minor phase differences between central and peripheral ROI-areas in the lungs do not generally disturb the analysis.

The basic idea, as described above, in calculating pulsating blood flow in the lungs is to equalize it with the summed area in one or more cycles in measured image series when the patient has been able to hold his breath. If the analysis is subjected to the entire image area, perfusion images with more disturbing noise in the surroundings around the lungs may be obtained.

The purpose of the submatrix analysis is to obtain a perfusion numerical map in which the distribution and amount of pulsating perfusion can easier be comprehended. It has been noted that the analysis based on a submatrix, for instance 6×6, results in an illustrative appearance of perfusion intensities while that of for example 16×16 analysis is too coarse.

In FIGS. 2a, 2b and 3a, 3b the grey scale perfusion images (figures a) and the numerical maps (figures b) analyzed by this invention are shown. It can clearly be appreciated that the lung perfusion of the healthy subject is smooth while the corresponding distribution of lung perfusion of the sick patient (clinically and scintigraphically proven PE) is very irregular and heterogeneous.

It has also been found that the lung perfusion in a normal volunteer varies little from one cycle to another. Patients with disturbance in the lung perfusion may on the other hand have uneven lung perfusion cycles, extra heart beats and other disturbances which may also be diagnosed with these measurements.

In grey shade perfusion image some central lung blood vessels and the traces of their movements can be seen. The perfusion signal even from behind the heart is detectable in slim patients.

Other oblique projections but the PA one can be taken to yield additional localizing information and to clarify other influencing factors.

The imaging method of this invention is very reliable when central areas of the lungs are measured. Areas in the lung periphery are thinner and contain less blood. Therefore the measured signal is weak and may arise problems in the interpretation. Uncertainty is also caused by the averaging analysis and the vagueness to determine the curve minima points based on the submatrix calculations. Generally speaking border areas have smaller significance in determining lung perfusion and the reliable measurement of the central areas obtained with this invention is sufficient for the diagnosis.

The method of this invention has been tested in different patient examinations, and it has been found to function properly. The analyzed images are clear and illustrative.

The method according to the invention can be modified in many ways while keeping within the inventive basic idea and the scope of the appended claims.

What is claimed is:

1. Method to determine lung perfusion with the fluoroscopic principle, characterized in that the transmitted X-ray radiation of the patient under examination is measured during at least one heart cycle using an image intensifier, the signal of the image intensifier is digitized, the signal is taken into a Personal Computer (PC) based device and analyzed.

2. Method according to claim 1, characterized in that perfusion curve from a user selected region of interest is calculated, two or more minima points are selected from the curve, the size of the submatrix in use is selected and used for the calculation of the amount of perfusion in each submatrix utilizing the entire image series and the sums of the signal from the images between the minima points are used to make up the perfusion image.

3. Method according to claim 2, characterized in that the obtained grey scale image of relative lung perfusion is normalized and further processed into a numerical map.

4. Method according to claim 1, characterized in that it is used X-ray radiation with high voltage and a thick copper filter.

5. Method according to claim 4, characterized in that the high voltage is about 100 kVp and the thickness of the copper filter is from about 1 mm to about 3 mm.

* * * * *